US009357975B2

(12) United States Patent
Baturin et al.

(10) Patent No.: US 9,357,975 B2
(45) Date of Patent: *Jun. 7, 2016

(54) LARGE FOV PHASE CONTRAST IMAGING BASED ON DETUNED CONFIGURATION INCLUDING ACQUISITION AND RECONSTRUCTION TECHNIQUES

(71) Applicant: Carestream Health, Inc., Rochester, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 14/143,254

(22) Filed: Dec. 30, 2013

(65) Prior Publication Data
US 2015/0182178 A1     Jul. 2, 2015

(51) Int. Cl.
*G03H 5/00*     (2006.01)
*G01N 23/00*     (2006.01)
*A61B 6/00*     (2006.01)
(Continued)

(52) U.S. Cl.
CPC ............... *A61B 6/484* (2013.01); *A61B 6/4035* (2013.01); *A61B 6/4291* (2013.01); *G01N 23/20075* (2013.01); *A61B 6/0457* (2013.01); *A61B 6/06* (2013.01); *A61B 6/5205* (2013.01); *A61B 6/54* (2013.01); *G01N 2223/427* (2013.01);
(Continued)

(58) Field of Classification Search
CPC ................ G03H 5/00; G21K 2207/00; G21K 2207/005; A61B 6/484; A61B 6/4291; A61B 6/4035; G01N 23/20075; G02B 5/20; G02B 5/201; G02B 5/207; G02B 5/28; G02B 5/02133; G02B 5/02142; G02B 9/00; G02B 9/02001; G02B 9/0201; G02B 9/02015; G02B 9/02017; G02B 9/02018; G02B 9/02029; G02B 9/0203; G02B 9/02041; G02B 9/020473; G02B 9/02085; G02B 9/0001
USPC .......................................................... 378/36
See application file for complete search history.

(56) References Cited

U.S. PATENT DOCUMENTS 9,001,967 B2* 4/2015 Baturin .................. A61B 6/484
                                                                378/156
2010/0246765 A1* 9/2010 Murakoshi ............. A61B 6/484
                                                                 378/62

(Continued)

FOREIGN PATENT DOCUMENTS

WO     2013/126296     8/2013

OTHER PUBLICATIONS

International Search Report, dated Feb. 5, 2014, International Application No. PCT/US2014/066027, 5 pages.
(Continued)

*Primary Examiner* — Anastasia Midkiff

(57) ABSTRACT

Embodiments of methods and apparatus are disclosed for obtaining a phase-contrast digital imaging system and methods for same that can include an x-ray source for radiographic imaging; a beam shaping assembly, an x-ray grating interferometer including a phase grating and an analyzer grating; and an x-ray detector; where the source grating, the phase grating, and the analyzer grating are detuned and a plurality of uncorrelated reference images are obtained for use in imaging processing with the detuned system.

19 Claims, 12 Drawing Sheets

(51) Int. Cl.
*G01N 23/20* (2006.01)
*A61B 6/04* (2006.01)
*A61B 6/06* (2006.01)

(52) U.S. Cl.
CPC .......... *G01N2223/6126* (2013.01); *G03H 5/00* (2013.01); *G21K 2207/005* (2013.01)

(56) References Cited

U.S. PATENT DOCUMENTS

| | | | |
|---|---|---|---|
| 2012/0163554 A1* | 6/2012 | Tada | A61B 6/4035 378/154 |
| 2013/0259194 A1 | 10/2013 | Yip et al. | |
| 2014/0226785 A1* | 8/2014 | Stutman | G01N 23/046 378/36 |
| 2015/0117599 A1* | 4/2015 | Yun | A61B 6/4291 378/36 |
| 2015/0216499 A1* | 8/2015 | Martens | G01N 23/20025 378/62 |

OTHER PUBLICATIONS

C. Kottler et al., "Grating Interferometer Based Scanning Setup for Hard X-ray Phase Contrast Imaging", American Institute of Physics, 2007, 78, pp. 043710-1-043710-4.

* cited by examiner

LARGE FOV PHASE CONTRAST IMAGING BASED ON DETUNED CONFIGURATION INCLUDING ACQUISITION AND RECONSTRUCTION TECHNIQUES

FIELD OF THE INVENTION

The application generally relates to digital x-ray imaging methods/systems, and more specifically, to methods and/or systems for acquiring multiple image information of an object (e.g., medical radiographic imaging) using a grating-based differential phase contrast imaging technique.

BACKGROUND

Conventional medical x-ray imaging devices employ absorption information to probe the interior structure of imaged objects. While generally good contrast between highly attenuating (e.g., hard) and weakly attenuating (e.g., soft) materials is observed, the separation between soft-tissue materials can be difficult because of a low relative contrast. For example, the low-contrast soft tissue materials include, but are not limited to vessels, cartilages, lungs, and breast tissues, which provide poor contrast in comparison to highly attenuating bone structures. In the recent years, interferometric x-ray imaging devices have been introduced to address soft-tissue imaging. In addition to conventional absorption, such devices can use the wave nature of x-ray radiation to measure diffraction of x-rays traversing the imaged object. As an electromagnetic wave, the x-ray can be characterized by its frequency, amplitude, and phase. When an x-ray, as an electromagnetic wave, penetrates a medium, its amplitude is attenuated and phase is shifted. The material dependent index of refraction can be represented as equation (1) below:

$$n = 1 - \delta + i\beta, \quad (1)$$

where the imaginary part $\beta$ contributes to the attenuation of the amplitude and the real part $\delta$ (refraction index decrement) is responsible for the phase shift. While the interferometer type of imaging devices can measure both $\beta$ and $\delta$ terms, the conventional x-ray imaging devices can detect only $\beta$. It is known that $\beta$ and $\delta$ are proportional to atomic scattering factors. For example, for a compound of density $\rho$ the refractive index, shown in equation (1), can be expressed in terms of the atomic scattering factors $f_1$ and $f_2$ as equation (2) below:

$$n \cong 1 - \frac{r_e N_a \lambda^2 \rho}{2\pi} \left( \sum_k x_k (f_{1,k} + i f_{2,k}) \right) \bigg/ \left( \sum_k x_k A_k \right), \quad (2)$$

where $r_e$, $N_a$, $\lambda$, and $\rho$ are the electron radius, Avogadro number, photon wavelength, and effective density of compound, respectively. The summation is taken over the relative concentrations $x_k$ of each of the chemical elements of atomic mass $A_k$ comprising the compound. Using equation (2), it can be shown that $\delta$ (rad/cm units) is about $10^3$ to $10^4$ times larger than $\beta$ (1/cm units). This provides a potential for imaging soft-tissue materials with higher contrast.

To date, several phase contrast imaging (PCI) techniques have been explored including: 1) the interferometer technique, 2) the diffraction-enhanced imaging (DEI) technique, and 3) the free-space propagation technique. However, there are various practical problems associated with all three techniques. In the case of crystal interferometers and diffractometers, high temporal coherence (i.e., a high degree of monochromaticity) is required, which, in result, limits the application to a synchrotron radiation or a well defined monochromatic radiation source. In addition to requirement of synchrotron source, the use of multi-hole collimator in DEI limits the achievable spatial resolution and increases the acquisition time. The free-space propagation technique can be limited in efficiency because of a requirement of high spatial coherence, which only can be obtained from an x-ray source with a very small focal spot size, or large propagation distance.

Further, grating based interferometer devices can be used for differential phase contrast imaging. Such imaging devices can include standard broadband x-ray source, beam shaping assembly including a collimator, three gratings (source G0, phase G1, and absorption G2 gratings), and x-ray detector; where the three gratings are positioned in such a way that their plane and the grating bars are aligned to each other. Alternatively, a microfocus X-ray source or synchrotron radiation source can be used instead of grating G0 and a large incoherent X-ray source.

Commonly accepted acquisition techniques for grating based PCI systems can use a controlled displacement during imaging of one of the three gratings relative to each other over the period of grating structure of absorption grating G2, which is typically few microns (e.g., 2 μm). Such an acquisition technique can be referred to as a phase stepping technique. Typical value of one displacement or step in such an acquisition is in the order of few hundred nanometers (e.g., 250 nm-500 nm). Although piezoelectric actuators, which can be used for grating displacement, can reach 10's of nanometer precision, the piezoelectric actuators are not linear (e.g., the relationship between displacement, x, and applied voltage V is not linear). To obtain high quality image reconstruction, the displacement Δx needs to stay constant during stepping, which requires unequal voltage increments, ΔV, at each step. Repeatability or optimization of such a system configuration can require thorough calibration, which prescribes the nominal voltage values at each step. Alternatively, a position sensitive feedback system can be used to linearize the voltage versus displacement characteristic. In addition, thermal expansion and/or compression of flexures holding the stepping grating can easily result in displacement of over a hundred of nanometers per Celsius degree. Thus, good thermal stability during an image acquisition time can be required. Accordingly, there is a long felt need for improvements to grating based PCI systems and/or methods for using the same.

SUMMARY OF THE INVENTION

An aspect of this application is to advance the art of medical digital radiography.

Another aspect of this application is to address, in whole or in part, at least the foregoing and other deficiencies in the related art.

It is another aspect of this application to provide, in whole or in part, at least the advantages described herein.

An aspect of this application is to provide methods and/or apparatus to address and/or reduce disadvantages caused by the use of PCI imaging apparatus and/or methods using the same.

An aspect of this application is to provide x-ray interferometer devices and/or methods for differential phase contrast imaging based on the Talbot-Lau three-grating configuration. Another aspect of the application is to provide methods and/or apparatus embodiments for detuned PCI medical imaging.

Another aspect of the application is to provide methods and/or apparatus embodiments for applications including but not limited to medical imaging, non-destructive testing, and national security (e.g., baggage or cargo scanning). Another aspect of the application is to provide methods and/or apparatus embodiments for full width or large field of view (FOV) phase contrast imaging (PCI) (e.g., greater than 50 mm square).

Another aspect of the application is to provide imaging methods and/or apparatus embodiments that can provide a large FOV phase-contrast digital imaging system that can include a polychromatic x-ray source; a beam shaping assembly including a collimator, a source grating, an x-ray grating interferometer including a phase grating and an analyzer grating; and an area x-ray detector; where a plurality of uncorrelated reference images are obtained for use in imaging processing with the detuned system.

Another aspect of the application is to provide imaging methods and/or apparatus embodiments that can provide reconstruction methods including subsequent digital shifting of the images of individual x-ray exposures (or images at each step) in such a way that effects of the stationary object and moving moiré fringe pattern can be achieved. One exemplary reconstruction embodiment can produce an absorption image, dark field image, differential phase image, and integrated phase image.

Another aspect of the application is to provide imaging methods and/or apparatus embodiments that can provide full width FOV radiographic phase contrast imaging, and/or can be built in tiled configuration, and/or use scan by parts (e.g., image stitching) acquisition where a plurality of tiles are used or one or more tiles is used in a plurality of positions.

In accordance with one embodiment, the present invention can provide a method executed at least in part on a computer that can include providing a beam shaping assembly; providing an x-ray grating interferometer comprising a phase grating G1, and an analyzer grating G2; offsetting a pitch of the analyzer grating G2 relative to a pitch of an interference pattern produced by the phase grating G1 at a prescribed distance from the phase grating G1 to generate a repeatable fringe pattern; repeatedly exposing an object using an x-ray source while moving the object relative to at least one cycle of the fringe pattern to generate a set of image data; and taking a plurality of reference images by an x-ray detector.

In accordance with one embodiment, the present invention can provide a digital radiographic (DR) phase-contrast imaging (PCI) system including a beam shaping assembly including a source grating G0; an x-ray grating interferometer including a phase grating G1, and an analyzer grating G2; and an area x-ray detector; where a pitch and a position of the analyzer grating G2 relative to a pitch of an interference pattern produced by the phase grating G1 produce a repeated fringe pattern over a width of the analyzer grating G2, and where the relative position of the phase grating G1 and the analyzer grating G2 does not change for an image scan of an object, where the object is configured to move relative to the repeated fringe pattern during the scan, where the x-ray detector is configured to generate a plurality of uncorrelated reference images used in a DR PCI image reconstruction.

In accordance with one embodiment, a microfocus X-ray source or synchrotron radiation source can be used instead of grating G0 and a large incoherent X-ray source.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

DESCRIPTION OF EXEMPLARY EMBODIMENTS

Figure 1:
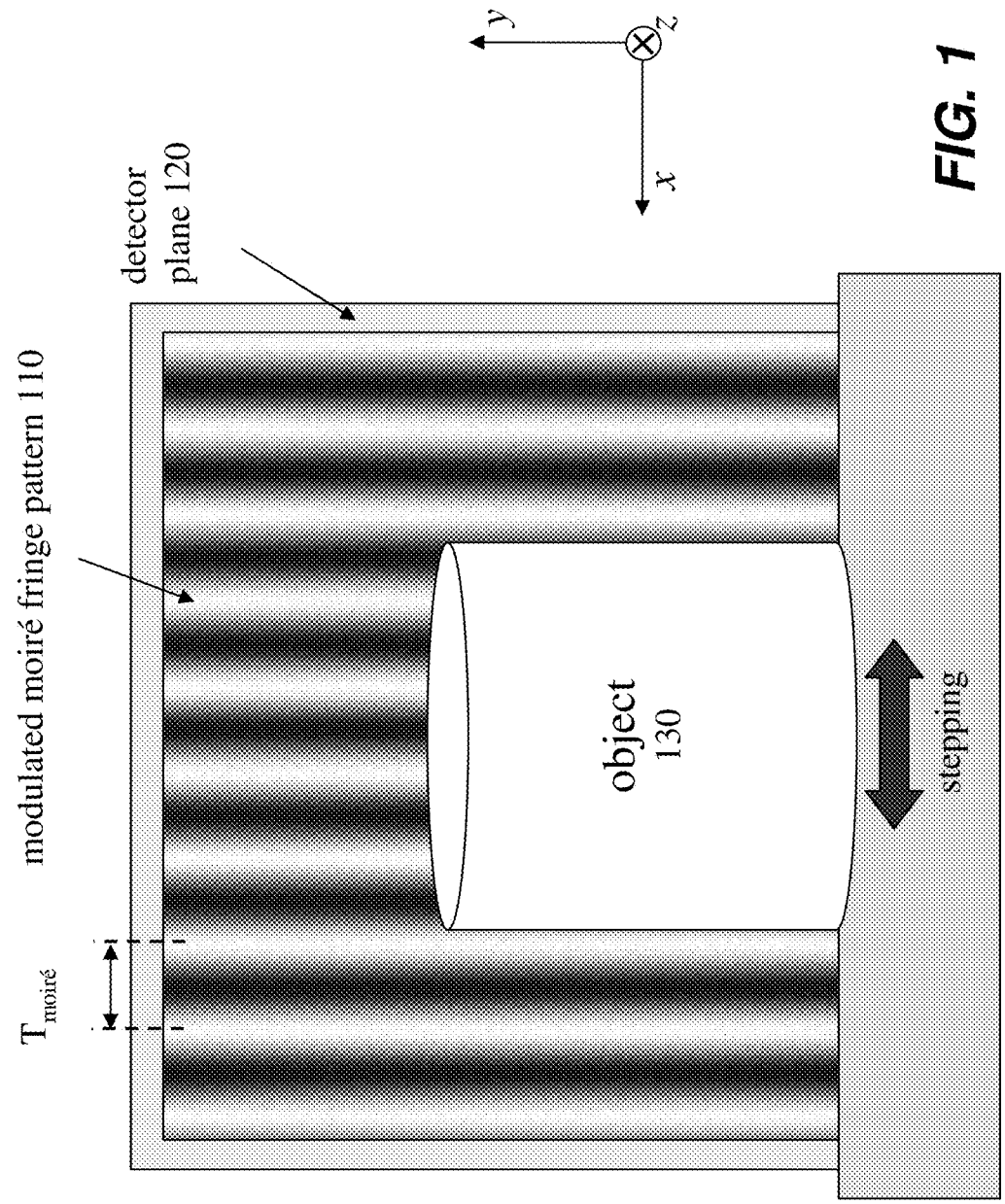
FIG. 1 is a schematic diagram that shows an exemplary modulated moiré fringe pattern in a plane of a radiographic detector and exemplary relative position and displacement direction of an imaged object according to embodiments of the application.

The following is a description of exemplary embodiments of the invention, examples of which are illustrated in the accompanying drawings. Wherever possible, the same reference numbers will be used throughout the drawings to refer to the same or like parts.

For illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention may have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Certain exemplary embodiments described herein for grating based interferometer devices and/or methods can be used for differential phase contrast imaging. An exemplary imaging device can include a standard broadband x-ray source, a beam shaping assembly including a beam shaping apparatus (e.g., collimator), a plurality of gratings (e.g., source grating G0, phase grating G1, and absorption grating G2) positioned so that their respective planes and grating bars can be aligned (e.g., parallel) to each other. Preferably, a spatial positioning of an x-ray detector can be aligned to the gratings. Certain exemplary embodiments disclosed herein can provide a large field of view (FOV) (e.g., greater than 50 mm square) radiographic imaging of objects for applications including but not limited to medical, non-destructive test (NDT), and security (e.g., baggage or cargo scanning). Certain exemplary embodiments disclosed herein can provide an acquisition technique where relative positions of the gratings do not change, e.g., a phase stepping mechanism among the three gratings is not invoked. Thus, in some exemplary embodiments all three gratings (e.g., G0, G1, G2 can be fixed in space with respect to each other), fixedly move across objects, or alternatively, objects move across the spatially-fixed grating positions, over a period of at least one moiré fringe pattern modulated at (e.g., in the plane of) an x-ray detector. In exemplary embodiments, the period of moiré pattern can be easily larger than 1 mm, or the size of an imaging step can be few hundreds microns. Such displacement is much coarser in comparison to phase stepping techniques, and therefore other types of linear displacement stages, for example (but not limited to) linear motor, lead screw with motor, or stepper motor can be used for embodiments according to the application. Further, the sensitivity of the grating based interferometer device and/or method embodiments herein to temperature change may not be an issue or significantly effect diagnostic imaging.

Certain exemplary embodiments described herein for grating based interferometer devices and/or methods can be used for differential phase contrast imaging. FIG. 1 is a diagram that shows relative displacement between a PCI moiré fringe pattern and an object to be imaged. As shown in FIG. 1, exemplary imaging devices and/or methods can take advantage of a moiré fringe pattern 110 formed in a plane 120 of an x-ray detector, as shown in FIG. 1, to extract three images: 1) absorption, 2) dark-field, and 3) differential phase. Integration of the differential phase image in the direction perpendicular to moiré fringe pattern (e.g., in x-direction, as shown in FIG. 1) can result in a complimentary integrated phase image. Relative motion (e.g., stepping) of an object 130 can be performed over or cover at least one period of moiré fringe pattern $T_{moiré}$ modulated in the plane 120 of x-ray detector.

Figure 2:
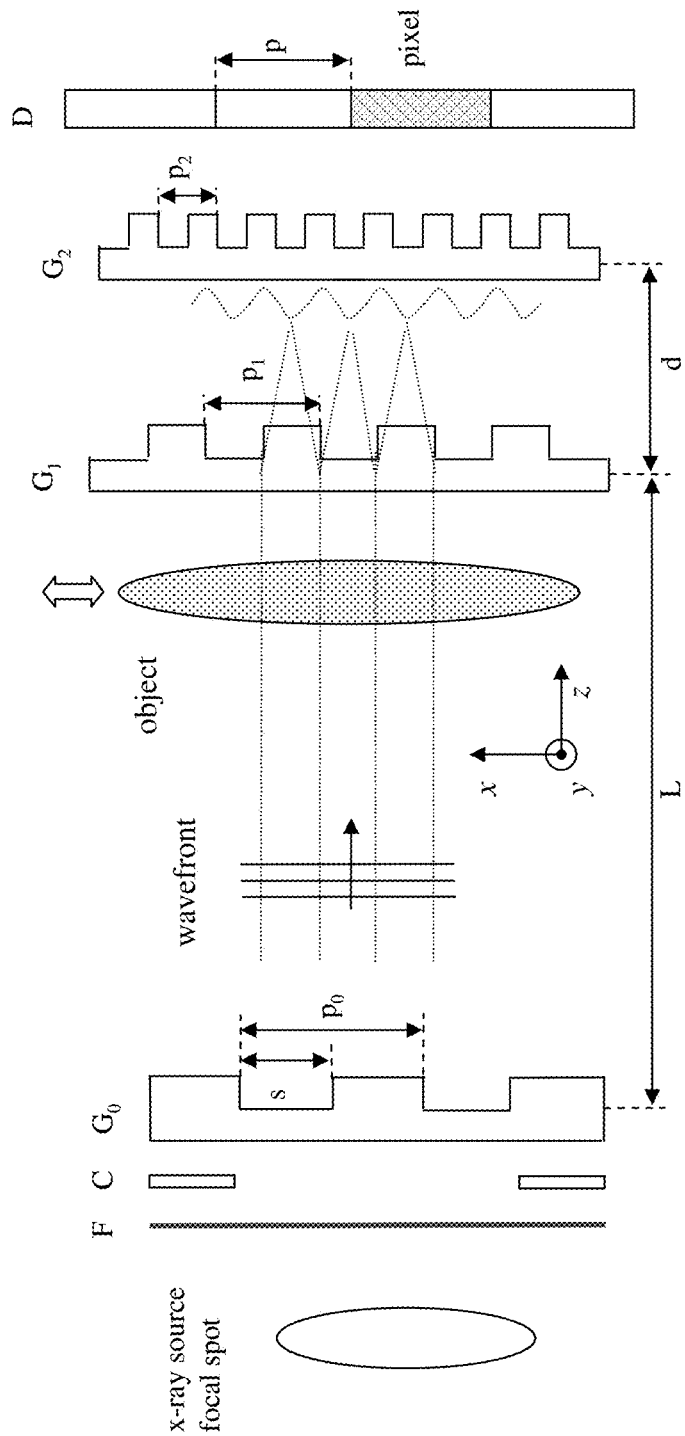
FIG. 2 is a diagram that shows schematics of an exemplary detuned three-grating PCI system with stationary or fixed G0, G1, and G2 gratings where an object is configured to move relative thereto according to embodiments of the application.

FIG. 2 is a diagram that shows a schematic of an exemplary three-grating phase contrast imaging system embodiment (e.g., radiographic interferometer). Three gratings, namely, source grating G0 including absorbing gold bars, phase grating (or beam splitter) G1 including silicon bars, and analyzer grating G2 including absorbing gold bars can be used. The gratings can be made on silicon wafers using standard photolithography techniques, with subsequent electroplating to cover or fill the grooves with gold (e.g., G0 and G2). Other materials can be used instead for G0, G1, G2 gratings fabrication as known to one skilled in the art. As shown in FIG. 2, D can be an x-ray detector, F can be optional additional filtration and C can be a beam shaping apparatus or collimator. The plane and grating bars of these three gratings G0, G1, G2 can be parallel to each other. The source grating G0 can be placed close to a radiation source or x-ray source (not shown). The second grating G1 and the third grating G2 can have a fixed distance d in between, for example, by being mechanically coupled together, electromechanically connected or rigidly coupled together. Similarly, the source grating G0 and the interferometer (G1, G2, and D) can be coupled to have a variable, but known or fixed distance L between them.

The source grating G0 can allow the use of a large incoherent x-ray source by creating an array of individually coherent line sources that can provide sufficient spatial coherence for the interferometric contrast. The phase grating G1 can operate as a beam splitter and divide the incoming beam essentially into the ±1 diffraction orders. These two ±1 diffracted beams can interfere and form a periodic interference pattern in the plane of the grating G2 through the Talbot self-imaging effect. When an object is inserted in the x-ray beam path, the position of the moiré fringe pattern would change because of x-ray diffraction in the object. As the change of the moiré fringe position in the micron range is not determined with a common x-ray detector, an analyzer grating G2 can be placed at a specific Talbot distance from the phase grating G1 to form moiré fringe pattern in the plane of x-ray detector D located directly behind the grating G2.

The conventional phase stepping acquisition technique, which allows intensity modulation in the plane of an x-ray detector, involves displacement (in a form of stepping) of one of the gratings with respect to another grating (e.g., stepping the G2 grating along x axis relative to the phase grating G1). As a result of stepping the G2 grating along the x axis relative to the phase grating G1, the periodic sine or cosine intensity curve can be measured by the x-ray detector at each pixel location, which allows subsequent image reconstruction.

Contrary to the conventional phase stepping technique, exemplary embodiments according to the application described herein can use an alternative acquisition technique, which can take advantage of the periodic structure of the moiré fringe pattern. According to exemplary embodiments of the application, the gratings and x-ray detector can be at rest and fixed in space with respect to each other, while the imaged object is moved across (e.g., stepped across in direction of x axis), or vice versa (e.g., object is at rest and the gratings with detector that are fixed in space with respect to each other, can be stepped across the object). Configurations where the moiré fringe pattern is generated or can be observed are referred to herein as a "detuned" configuration.

Figure 3:
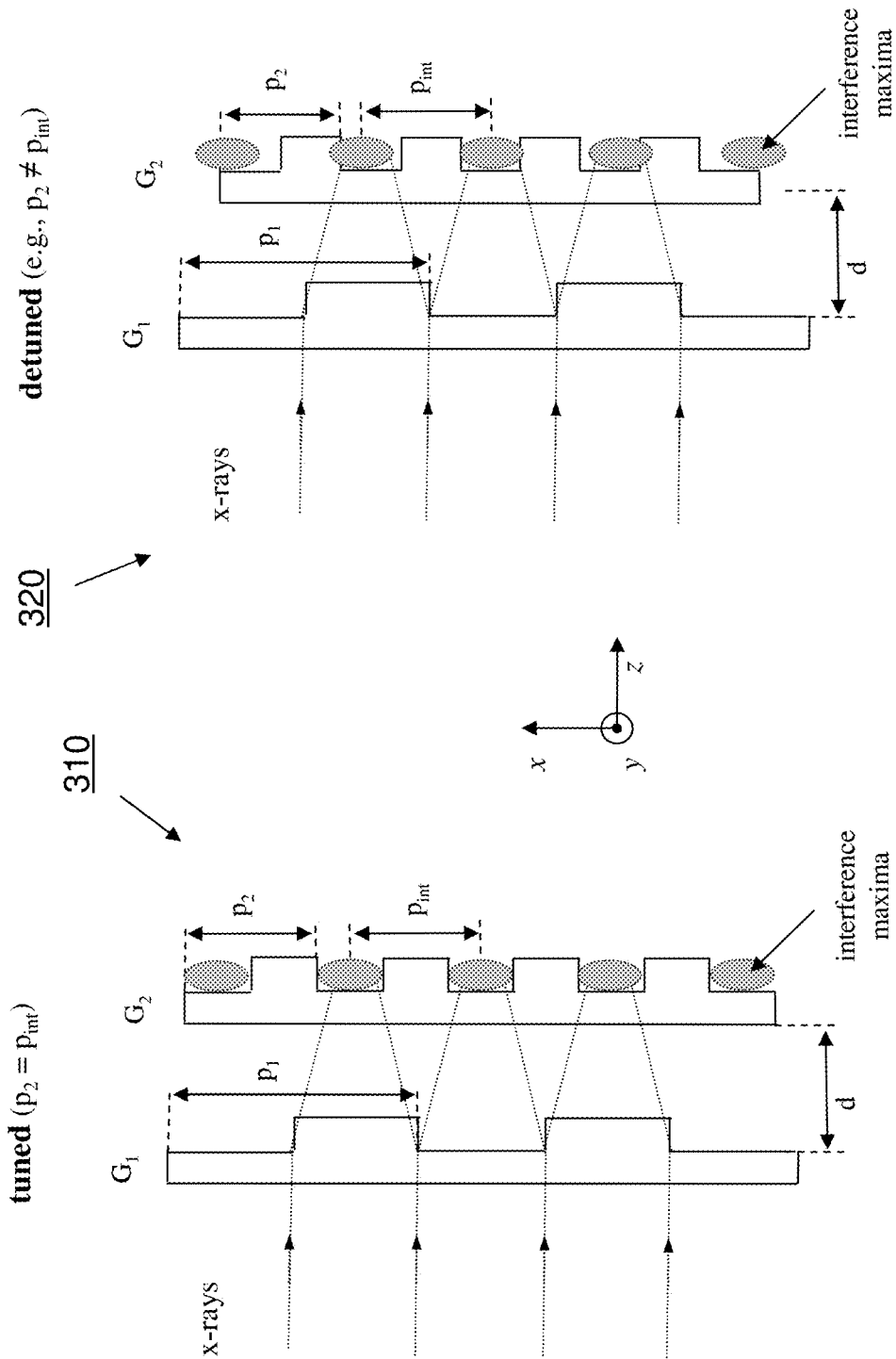
FIG. 3 is a diagram that shows schematics of the tuned and detuned configurations of the phase contrast imaging system according to embodiments of the application.

For certain exemplary embodiments herein, a detuned system can be understood as a grating based interferometer system in which the pitch $p_2$ of the analyzer grating is purposely set to be not equal to the period of interference pattern $p_{int}$ formed in the plane of analyzer grating. FIG. 3 is a diagram that shows exemplary schematics of a tuned configuration 310 and a detuned configuration 320 of a phase contrast imaging system. The analyzer grating and the interference pattern can be approximated as a cosine (or sine) waves with the frequencies $f_2=1/p_2$ and $f_{int}=1/p_{int}$, respectively. Then, the signal $I_s$ measured by detector, is:

$$I_s = MTF(f) \cdot [\cos(2\pi f_{int} x) \cdot \cos(2\pi f_2 x)] = MTF(f) \cdot [\cos(2\pi (f_{int}+f_2)x) + \cos(2\pi (f_{int}-f_2)x)]/2. \quad (3)$$

The spatial frequency at $p_2=2$ μm pitch of the analyzer grating is 500 cyc/mm. When summed with comparable frequency of interference pattern, it can double, e.g., $f_{int}+f_2=1000$ cyc/mm. The value of $f_0$ in indirect charge integrating detectors can typically be between 1 and 2 cyc/mm. Therefore, detector will generally measure no signal at 1000 cyc/mm. Then, the only detectable signal would be:

$$MTF(f) \cdot \cos(2\pi (f_{int}-f_2)x)/2. \quad (4)$$

Figure 4:
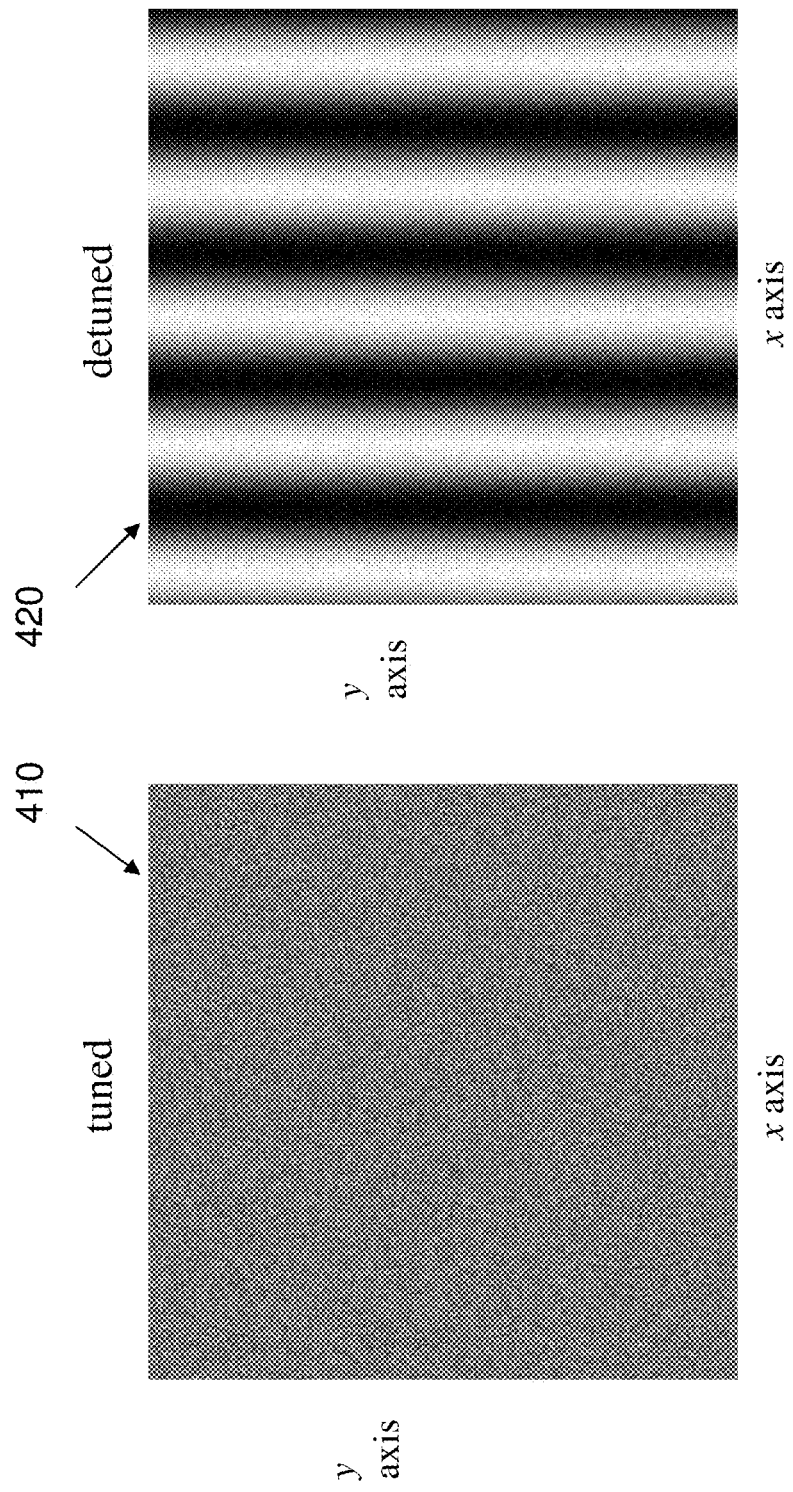
FIG. 4 is a diagram that shows examples of open field images respectively measured in a detector plane for tuned and detuned configurations of a PCI system according to embodiments of the application.

In the case of a tuned phase contrast imaging system ($f_{int}=f_2$), the signal is maximum. When measuring the open field in such configuration, a detected image at the detector yields the uniform image. In the case of detuned system, a detected image at the detector can have a cosine pattern. FIG. 4 is a diagram that shows an exemplary image of the uniform open field image 410 acquired by a tuned PCI system and an exemplary image of the fringe pattern of the open field image 420 acquired by a detuned PCI system.

Figure 5:
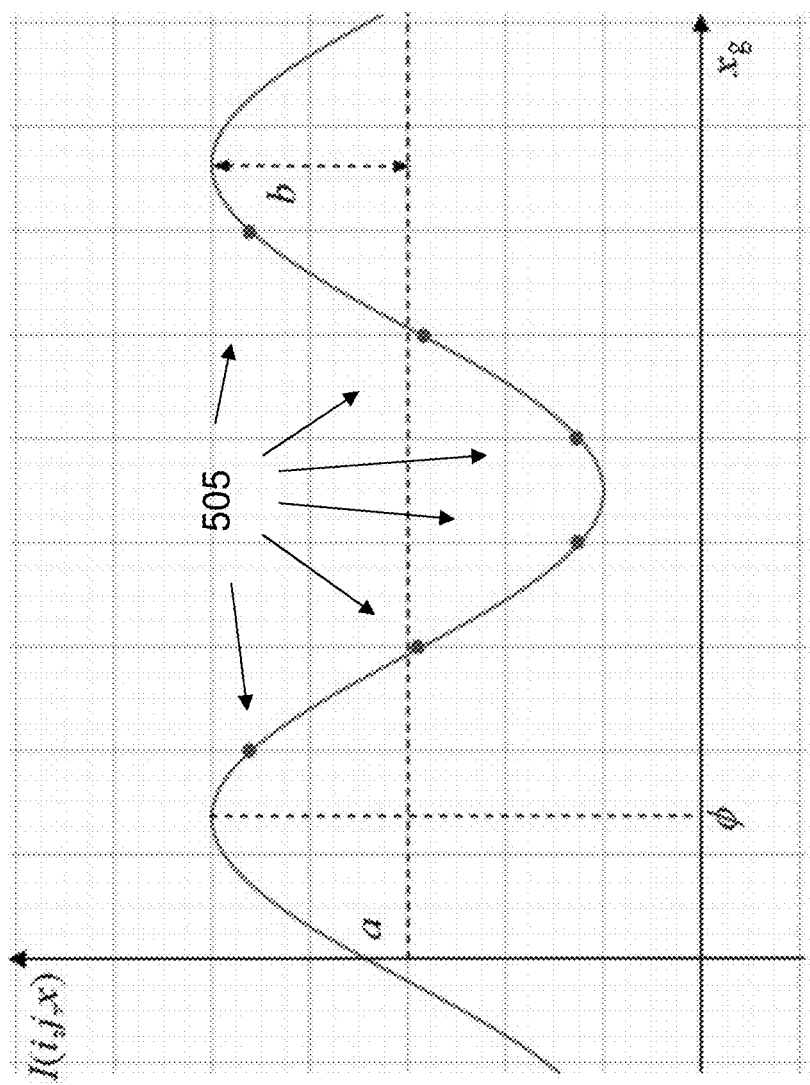
FIG. 5 is a diagram that shows an exemplary intensity curve formed by a conventional phase stepping technique for a tuned configuration of a PCI system.

FIG. 5 is a diagram that shows an exemplary intensity curve formed by a conventional phase stepping technique for a tuned configuration of a PCI system. The conventional phase stepping acquisition technique requires multiple x-ray exposures at different lateral positions $x_g$ (e.g., in x-axis) of analyzer grating G2 relative to the phase grating G1 (or relative displacement of one among the three gratings), which allows forming a cosine (or sine) shaped intensity curve shown in FIG. 5 (e.g., points 505 on the plot are examples of data points). For each pixel (i,j), such a signal oscillation curve (or intensity curve) can be expressed by a Fourier series:

$$I_s(i, j, x_g) \approx a_s(i, j) + b_s(i, j)\cos\left(\frac{2\pi}{p_2}x_g + \phi_s(i, j)\right), \quad (5)$$

$$I_b(i, j, x_g) \approx a_b(i, j) + b_b(i, j)\cos\left(\frac{2\pi}{p_2}x_g + \phi_b(i, j)\right). \quad (6)$$

Here, Equation (5) can represent the intensity measurement with object present, while Equation (6) can refer to a measurement without an object (or reference scan). Applying Fourier analysis technique, the following images can be obtained:

1) Transmission Image:

$$T(i, j) = \frac{a_s(i, j)}{a_b(i, j)}, \quad (7)$$

2) Dark-Field Image:

$$V(i, j) = \frac{b_s(i, j)/a_s(i, j)}{b_b(i, j)/a_b(i, j)}, \quad (8)$$

3) Differential Phase Contrast Image:

$$\left(\frac{\partial \Phi}{\partial x}\right)_{i,j} = \frac{p_2}{\lambda d_n}(\phi_s(i, j) - \phi_b(i, j)), \quad (9)$$

4) Integrated Phase Contrast Image:

$$\Phi_{i,j} = \frac{p_2}{\lambda d_n}\int (\phi_s(i, j) - \phi_b(i, j))dx. \quad (10)$$

These four different images of the object can be derived from the same data set and can be complementary to each other to provide multiple information of the object, which can enable the visualization of subtle details in the object.

Figure 6:
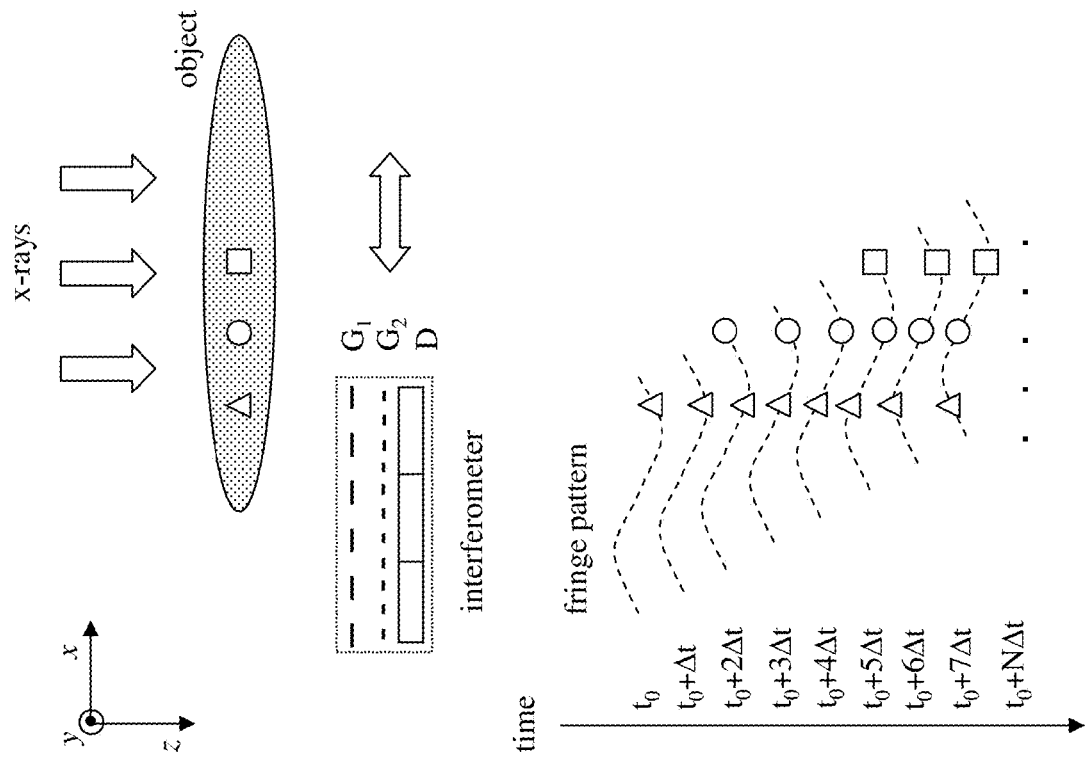
FIG. 6 is a diagram that shows schematics of object scan that project individual slices of the object onto moiré fringe pattern (one-period fringe is shown as an example) measured in the detector plane according to embodiments of the application.
Figure 7:
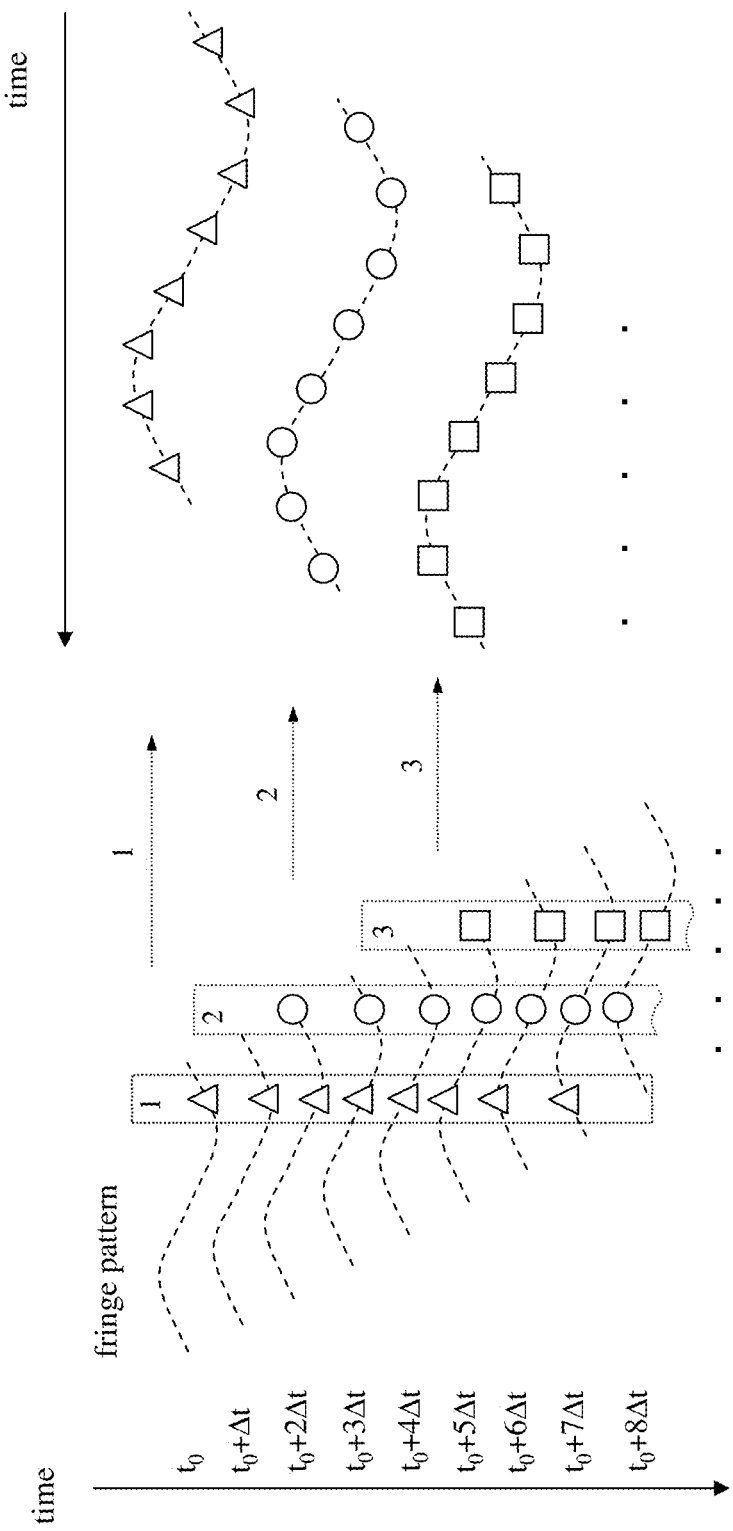
FIG. 7 is a diagram that shows schematics of image formation mechanism that retrieves the intensity curves of individual slices of scanned object according to embodiments of the application.

In detuned configurations, exemplary acquisition technique embodiments can take advantage of modulated moiré pattern in the plane of x-ray detector. FIG. 6 shows schematics of an object projection onto a PCI moiré fringe pattern as a result of relative motion between the object and an interferometer. As shown in FIG. 6, the triangle, circle, and square shapes in the exemplary schematics refer to different parts of the object. Thus, certain exemplary embodiments can provide for relative motion only between an object and an interferometer. In one embodiment, the gratings G1 and G2 and detector D (shown as interferometer) can be fixed at one relative position, for example rigidly attached to an arm, and the arm (or interferometer) can be moved (or stepped) across the stationary object. In alternative embodiments, the arm (or interferometer) can be at rest and the object can be laterally moved across in a plane perpendicular to incident x-rays. Further, the source, beam shaping assembly, and G0 grating can be stationary or can be coupled to an interferometer arm. When the object and the arm with fixed G1, G2, and D are moved relative to each other, those different parts of the object (e.g., the triangle, circle, and square shapes) can be individually projected on different lateral positions of the fringe pattern at subsequent instances of time. Thus, when the scan of the whole object is completed, each individual part of the object, such as triangle, circle and square, has preferably been measured several times (e.g., N=8) at different intensities through use of the fringe pattern. In other words, individual intensity curves (e.g., similar to one shown in FIG. 5 acquired by a conventional phase stepping technique) can be formed for each of the exemplary shapes (e.g., triangle, circle, and square). FIG. 7 is a diagram that shows an example of intensity curve formation for an individual slice of the object (e.g., triangles, circles, and squares) through use of the fringe pattern according to one embodiment of the application. The Fourier based reconstruction technique, described earlier, can be applied to each of the intensity curves to form the transmission, dark-field, differential phase, and integrated phase images for each of the slices. Then, the slice images can be combined or stitched together to form an image of the full object.

Figure 8:
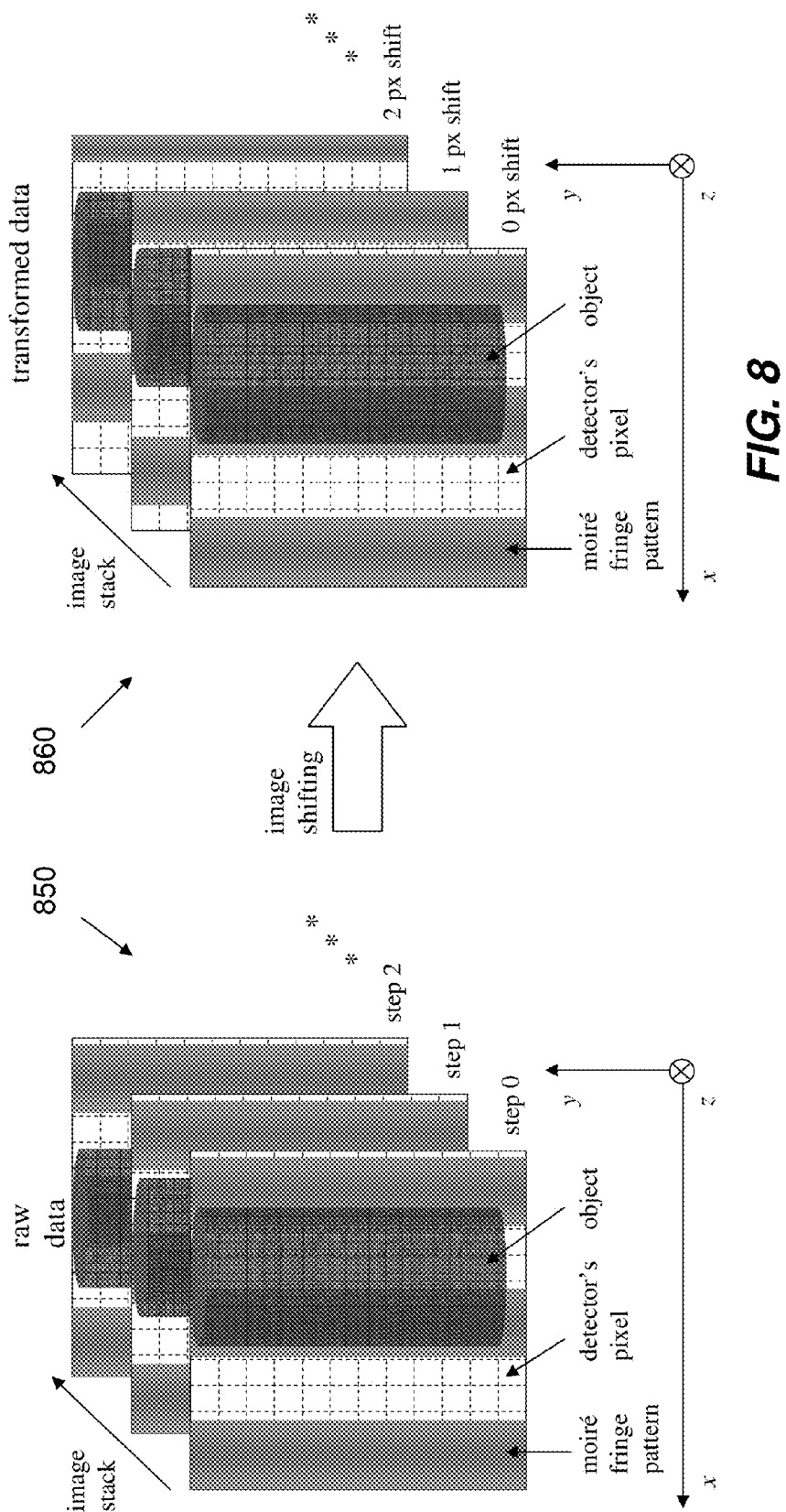
FIG. 8 is a diagram that shows schematics of object stepping relative to moiré fringe pattern (left) and image transformation (right) according to embodiments of the application.

In certain exemplary embodiments of large FOV configurations, where there can be many moiré fringe patterns present in the detector plane, an image shifting approach can be more appropriate in contrast to slice-by-slice image stitching with a single fringe pattern (e.g., shown in FIG. 7). FIG. 8 schematically displays an exemplary embodiment of image acquisition and shifting transformation used for image reconstruction according to embodiments of the application. Images 850 (called "raw data") show examples of data collected with all the gratings and detector (e.g., interferometer) being at rest and an object moving across the interferometer (e.g., in direction of x-axis) with step=$np_x/M$, where n is an integer number (1, 2, 3, ...), $p_x$ is a detector's pixel pitch and M is an image magnification (in FIG. 8, n=1). As was described herein, the same dataset can be obtained using an embodiment where the arm, which holds all gratings and detector (e.g., and x-ray tube), moves across the stationary object. Both motions can result in the same digital data: stationary fringe pattern(s) and moving object(s). Images 860 shown in FIG. 8 (called "transformed data") were incrementally offset (e.g., digitally shifted) by $np_x$. Such a shifting can create the effect of a stationary object, and the fringe pattern moving across the stationary object. As shown in FIG. 8, n=1 however, other values for n and M can be used. For example, when n=2, the sequence of image shifting can be: 1-st image stays the same, second image shifts by 2 pixels, third image shifts by 4 pixels, and etc.

For certain exemplary embodiments, reference images can be collected prior to or after the object scan, or the reference images can be stored in advance and then read out (e.g., from look-up table (LUT) or the like). In one embodiment, a number of reference images that can be used for proper reconstruction can be at least equal to the number of sample (or object) images. For example, when there were 8 images of sample collected during the scan of the object, the same number (e.g., 8) of reference images can preferably be acquired without the object. Further, position of all the gratings can be the same for all reference (or open field) images. As described in exemplary embodiments herein, the raw data can represent the motion of object with respect to stationary moiré fringe pattern, and the shifting transformation results in moiré pattern moving across the stationary object. If, for example, in comparison to 8 object scans only one reference image is acquired, the shifting transformation would require 8 copies (e.g., shifted) of the same reference image. Usage of such shifted copies of a reference image in the reconstruction procedure can result in increased noise or structured noise in all reconstructed images (e.g., transmission, dark-field, and differential phase) caused by noise correlation in shifted reference image copies. That is why in exemplary embodiments, a number of reference images should be sufficient to reduce correlated noise among the reference images used in reconstruction (e.g., shifted reference images). In one embodiment, the number of reference images should not be less than the number of object images, since in such a case the correlated noise can be reduced or eliminated.

Exemplary image shifting transformations can result in an image stack (or data) such as image stack 860, where each pixel along the image stack experiences cosine (or sine) oscillation (e.g., intensity curve shown in FIG. 5). In such a case, the Fourier reconstruction technique, described earlier, can be applied to extract transmission, dark-field, differential phase contrast, and integrated phase images according to embodiments of the application.

Figure 9:
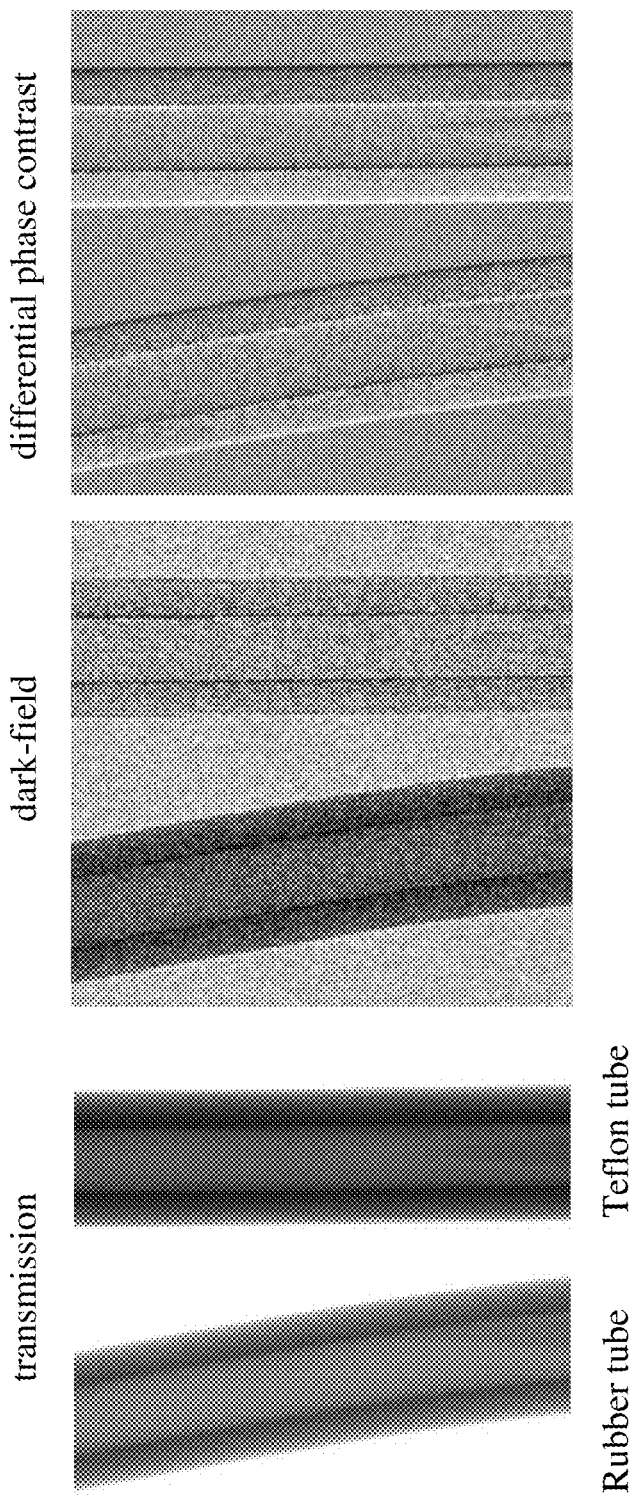
FIG. 9 is a diagram that shows an example of transmission, dark-field, and differential phase contrast images reconstructed from data collected by relative stepping of object over modulated moiré fringe pattern according to embodiments of the application.

FIG. 9 is a diagram that shows an example of transmission, dark-field, and differential phase contrast images reconstructed from large FOV PCI scans collected using a detuned configuration. As shown in FIG. 9, the object was moved relative to stationary interferometer with a step of ~120 µm. Caused by object magnification M≈1.058, a projected displacement of ~127 µm per one step was the result, which was equal to the pitch of detector. The images shown in FIG. 9 are for illustrative purposes and were not necessarily acquired using preferred or optimal imaging parameters, such as exposure, filtration, number of steps and etc.

Figure 10:
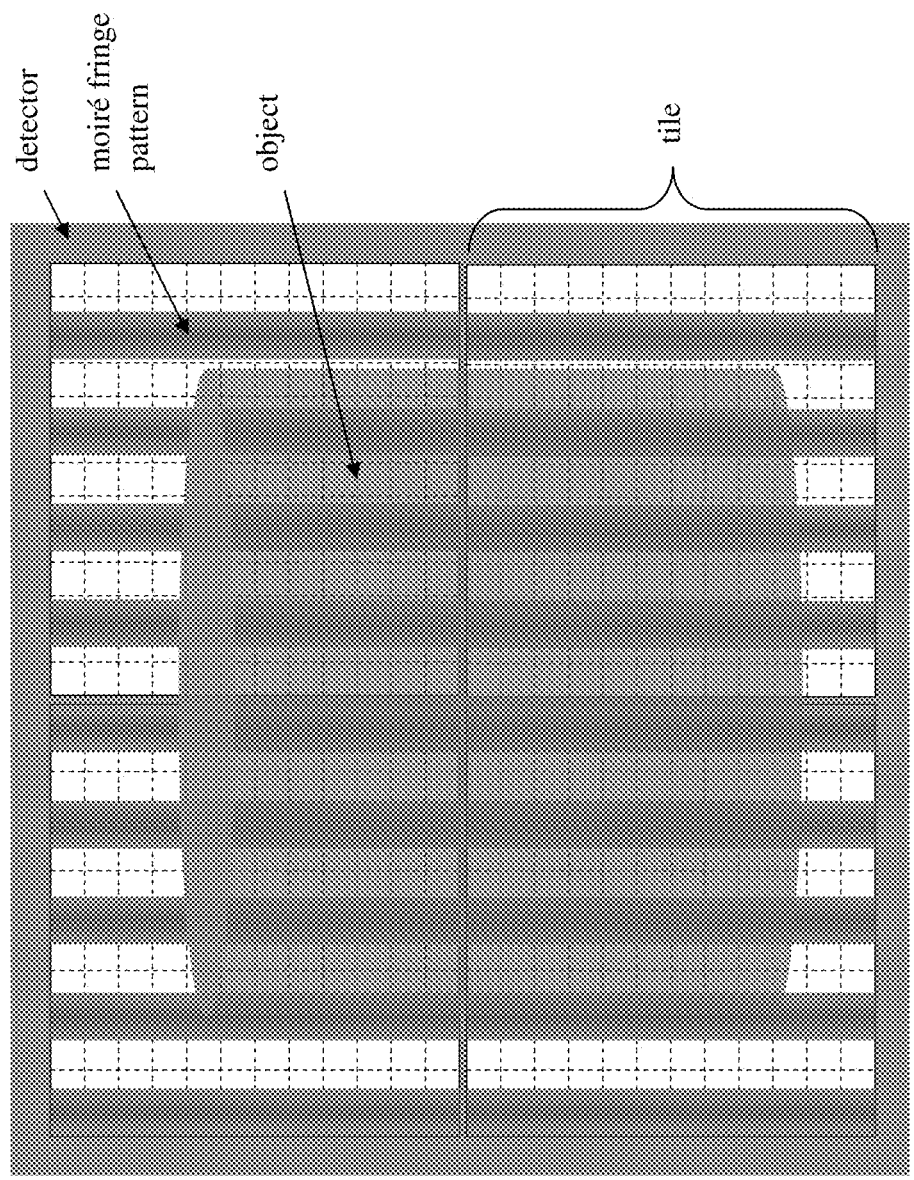
FIG. 10 is a diagram that shows an example of a tiled configuration for scanning an oversized object with dimensions exceeding the FOV of a single (G1+G2) tile (or interferometer) according to embodiments of the application.

When an object is larger or exceeds the grating's FOV, a tiled configuration embodiment can be used as shown in FIG. 10. However, the number of tiles can be less or more than shown in FIG. 10. Exemplary acquisition technique embodiments for a tiled configuration can include relative stepping (or motion) of object with respect to each of the plurality of tiles over at least one period of the moiré fringe pattern. Each tile can have rigidly connected G1 and G2 grating, spaced apart by a prescribed distance or an optimal distance (e.g., Talbot distance). Further, all tiles can share same x-ray tube, beam shaping assembly, G0 grating, and x-ray detector. However, the moiré fringes do not necessarily have to match in space (or be vertically aligned) when going from one tile to another among the plurality of tiles. For example, in one embodiment, each part of the image, corresponding to an individual tile, can be reconstructed independently from other tiles, and then the whole image can be stitched from all the reconstructed parts. Preferably, the frequency of the moiré fringe pattern among the plurality of tiles is as close to being the same as possible. Significantly unequal frequencies of the moiré fringe patterns among tiles can create artifacts (e.g., vertical stripes) in reconstructed images, since, in such a case, the number of points in intensity curves (e.g., see FIG. 5) might be different.

Figure 11:
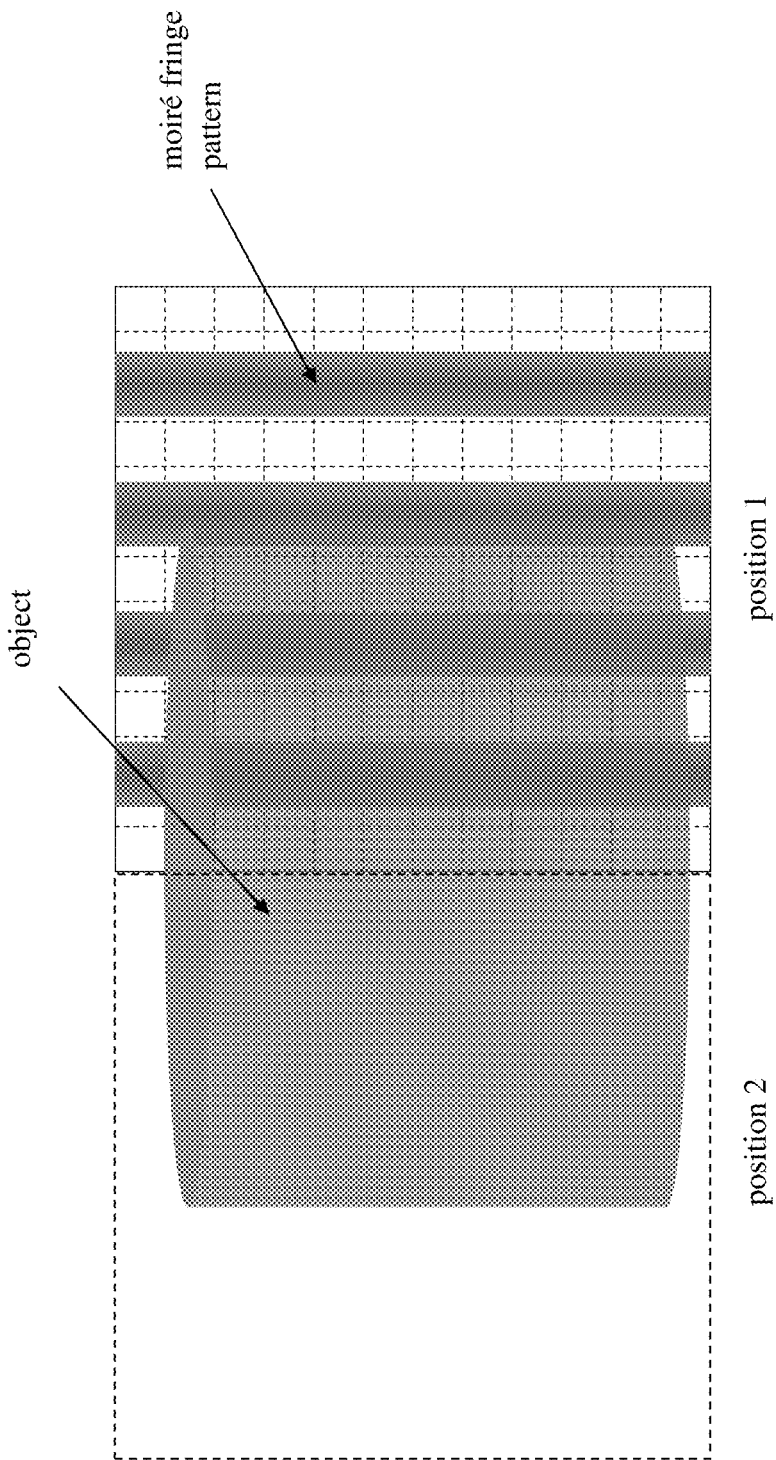
FIG. 11 is a diagram that shows an example of stitching configuration, where a first scan of part of the object is at interferometer position 1 and another scan for the remaining part of the object is at interferometer position 2 according to embodiments of the application.

The exemplary tiled configuration embodiment shown in FIG. 10 can potentially suffer from vignetting effect on one or more sides (e.g., in this case, left and right sides) caused by beam divergence. To reduce or avoid vignetting effects, one or more tiles (e.g., all) can be slightly tilted or include a slight bend to allow x-rays incident normally or substantially perpendicular to a tile surface. In an alternative embodiment, vignetting effects can be reduced or avoided by using only one interferometer (or tile), that can be moved for different positions (e.g., parts) of the object. Multiple imaging of an object using a single tile is illustrated in FIG. 11, where an interferometer scans the object first at position 1 and then scans the object at position 2, and then the image of the object can be stitched from the individual parts (e.g., two parts). However, embodiments of the application are not intended to be so limited, for example, exemplary stitching can also be done in different or vertical directions and can have more than 2 scan positions (e.g., for a single tile).

Figure 12:
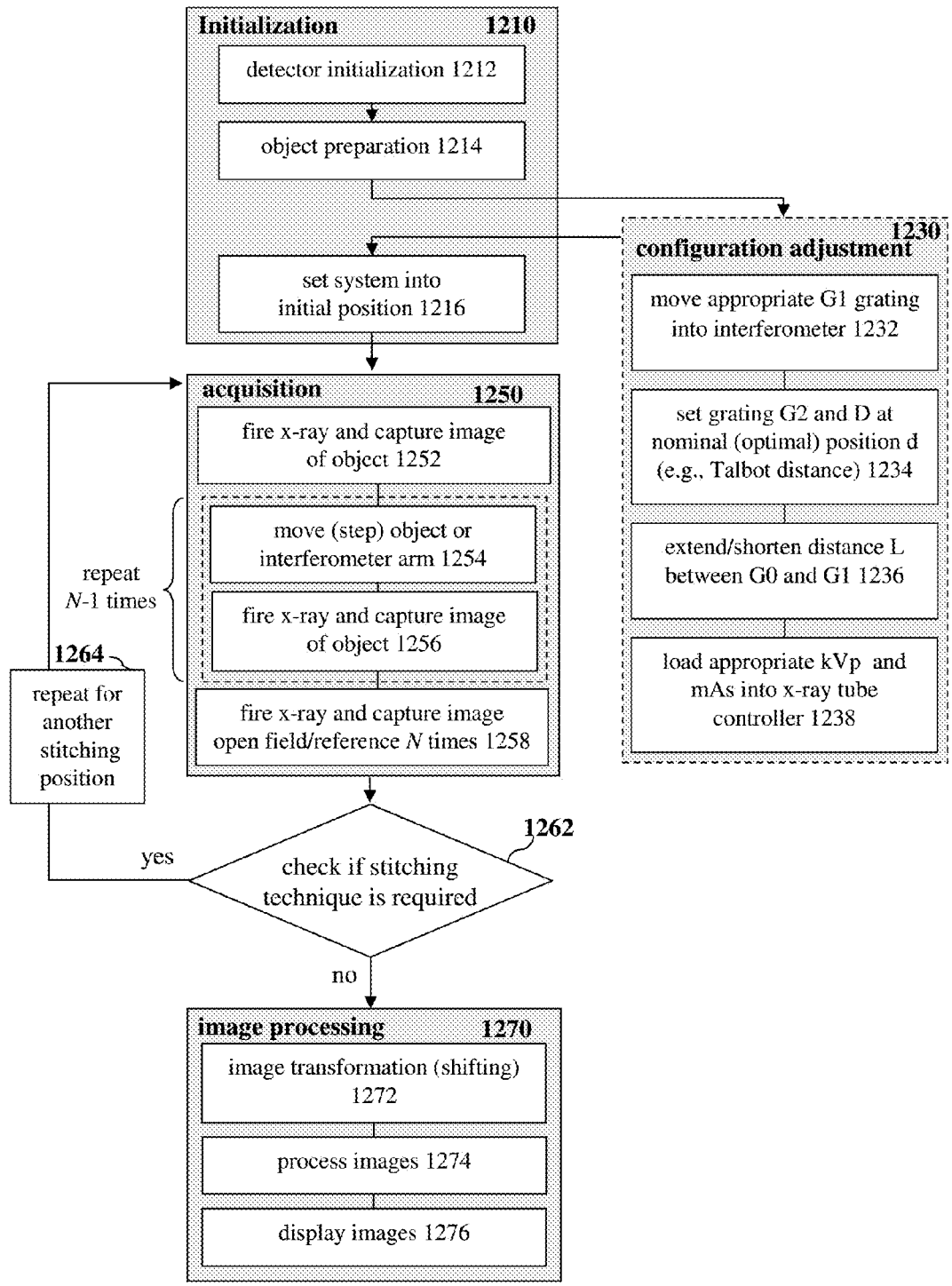
FIG. 12 is flow chart showing a method of operating a radiographic phase contrast imaging system according to embodiments of the application.

FIG. 12 is a flow chart that shows an exemplary method of operating a radiographic phase contrast imaging system according to embodiments of the application. As shown in FIG. 12, the method will be described using and can be implemented by embodiments of radiographic imaging apparatus shown in FIG. 8; however, the method of FIG. 12 is not intended to be limited thereby.

As shown in FIG. 12, system operations can include: 1) initialization 1210, 2) system configuration adjustment 1230, 3) acquisition 1250, and 4) image processing and reconstruction 1270 sections. In an initialization section 1210, detector can be initialized (e.g., warming up) in operation block 1212 and an object can be getting prepared according to preparation/handling regulations that can depend on the object and can differ for different object types (e.g., cartilage fixed in space or breast is compressed) in operation block 1214. Depending on desired imaging parameters, including radiation source conditions such as tube's voltage, a geometry (e.g., configuration) of PCI system can be adjusted using the configuration adjustment 1230 section. As shown in FIG. 12, exemplary processes for configuration adjustment 1230 can include moving or positioning an appropriate G1 grating into interferometer in operation block 1232, set grating G2 and D at nominal selected (e.g., optimal) position d (e.g., Talbot distance) in operation block 1234, extend/shorten distance L between G0 and G1 in operation block 1236, and load appropriate kVp and mAs into an x-ray tube controller in operation block 1238. However, more additional or fewer settings can be adjusted or included in exemplary configuration adjustment 1230. Then, the radiographic imaging system and/or the object can be set at an initial or "zero" position in operation block 1216.

As shown in FIG. 12, exemplary processes for acquisition 1250 can include imaging the object at an initial or "zero" position in operation block 1252. Then, relative motion of object with respect to fixed in space PCI gratings and the detector (e.g., interferometer) is implemented in operation block 1254 and the image can be taken at each position/step in operation block 1256. In total, the system can collect N data points. In one embodiment, the N data points can be collected by repeating operation blocks 1254, 1256 N–1 times. The relative object—interferometer displacement should at least cover one period of the moiré fringe pattern. Then, open field or reference images can be captured in operation block 1258. In one embodiment, N reference images can be captured in operation block 1258. If the stitching technique is to be used, for example because the size of the object exceeds the FOV of the system (operation block 1262, Yes), the interferometer part of the system can be moved into another position to cover one or more previously not-scanned areas of the object, and the stepping-and-expose sequence is repeated again (operation block 1264). Such a motion can be repeated until the whole object is imaged (operation block 1262, No). To avoid vignetting, the x-ray tube, beam shaping assembly, and G0 grating can be appropriately tilted each time when interferometer moves into another "stitching" position. When the appropriate object and reference images have been obtained, the method can continue to image processing 1270. Exemplary processes for image processing 1270 can include image transformation in operation block 1272, processing the transformed images in operation block 1274 and displaying or storing rendered images in operation block 1276. However, more additional or fewer operations can be adjusted or included in exemplary image processing 1270.

Exemplary embodiments herein can be applied to digital radiographic imaging panels that use an array of pixels comprising an X-ray absorbing photoconductor and a readout circuit (e.g., direct detectors). Since the X-rays are absorbed in the photoconductor, no separate scintillating screen is required.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of radiographic imaging systems and/or methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method, comprising:
providing an x-ray source for radiographic imaging;
providing a beam shaping assembly comprising a source grating G0;
providing an x-ray grating interferometer comprising a phase grating G1, and an analyzer grating G2;
providing an x-ray detector;
aligning the source grating G0, the phase grating G1, the analyzer grating G2, and the x-ray detector;
offsetting a pitch of the analyzer grating G2 relative to a pitch of an interference pattern produced by the phase grating G1 at a prescribed distance from the phase grating G1 to generate a repeating fringe pattern;
repeatedly exposing an object using the x-ray source while moving the object relative to at least one cycle of the fringe pattern to generate a set of image data, and while holding the x-ray source, the source grating G0, the phase grating G1, the analyzer grating G2, and the x-ray detector fixed relative to each other; and
capturing a plurality of images of the object by the x-ray detector.

2. The method of claim 1, further comprising transforming the set of image data to form a transformed image data set where the fringe pattern moves across the stationary object.

3. The method of claim 2, further comprising:
transforming a set of reference images equal in number or more to the set of transformed image data set; and
Fourier reconstructing the transformed image data set and the transformed reference images to at least one of extract transmission, dark-field, differential phase contrast, and integrated phase images of the object.

4. The method of claim 1, wherein the reference images are collected prior to or after the object scan, or the reference images are stored in advance of the object scan.

5. The method of claim 1, wherein the beam shaping assembly comprises a beam limiting apparatus and a source grating G0 or a microfocus X-ray source.

6. The method of claim 1, wherein moving the object relative to at least one cycle of the fringe pattern comprises stepping an object to move through the at least one cycle of the fringe pattern in a plane of the x-ray detector.

7. The method of claim 6, wherein a period of the repeatable fringe pattern is set to make the size of an imaging step greater than or equal to a pixel pitch of the x-ray detector or a fraction of the pixel pitch of the x-ray detector.

8. A method, comprising:
providing an x-ray source for radiographic imaging;
providing a beam shaping assembly;
providing an x-ray grating interferometer comprising a phase grating G1, and an analyzer grating G2;
offsetting a pitch of the analyzer grating G2 relative to a pitch of an interference pattern produced by the phase grating G1 at a prescribed distance from the phase grating G1 to generate a repeatable fringe pattern;
repeatedly exposing an object using the x-ray source while moving the object relative to at least one cycle of the fringe pattern to generate a set of image data; and
taking a plurality of reference images by an x-ray detector, wherein moving the object relative to at least one cycle of the fringe pattern comprises holding the interferometer and the x-ray detector fixed relative to each other while moving the object across the interferometer with a step=$np_x/M$, and wherein n is an integer number $(1, 2, 3, \ldots)$, $p_x$ is a detector's pixel pitch and M is an image magnification.

9. A method, comprising:
providing an x-ray source for radiographic imaging;
providing a beam shaping assembly;
providing an x-ray grating interferometer comprising a phase grating G1, and an analyzer grating G2;
offsetting a pitch of the analyzer grating G2 relative to a pitch of an interference pattern produced by the phase grating G1 at a prescribed distance from the phase grating G1 to generate a repeatable fringe pattern;
repeatedly exposing an object using the x-ray source while moving the object relative to at least one cycle of the fringe pattern to generate a set of image data; and
taking a plurality of reference images by an x-ray detector, wherein the x-ray source, the beam shaping assembly, the grating interferometer, and the detector are attached to a moving arm to operate together, and the moving arm performs a single FOV scan by exposing X sequential positions of the area x-ray detector to obtain a plurality of X raw images used to construct a 3D image, a distance between the X sequential positions=$np_x/M$, and wherein n is an integer number $(1, 2, 3, \ldots)$, $p_x$ is a detector's pixel pitch and M is an image magnification.

10. The method of claim 1, wherein a tiled configuration of interferometers is used in the radiographic imaging when an object is larger than a field of view (FOV) for each tiled interferometer.

11. The method of claim 1, wherein the repeatedly exposing an object larger than a field of view (FOV) of an interferometer using the x-ray source while moving the object relative to at least one cycle of the fringe pattern to generate a set of image data comprises:
performing multiple imaging of an object using a single x-ray grating interferometer, wherein an interferometer scans the object at a first position and then scans the object at a second position; and
stitching together the image of the object from the interferometer scan of the object at the first position and the interferometer scan of the object at the second position.

12. A digital radiographic (DR) phase-contrast imaging (PCI) system comprising:
an x-ray source;
a beam shaping assembly comprising a source grating G0;
an x-ray grating interferometer comprising,
a phase grating G1, and
an analyzer grating G2; and
an area x-ray detector;
wherein a pitch and a position of the analyzer grating G2 relative to a pitch of an interference pattern produced by the phase grating G1 produce a repeated fringe pattern over a width of the analyzer grating G2, the relative position of the x-ray source, the source grating G0, the phase grating G1 the analyzer grating G2, and the x-ray detector does not change for an image scan of an imaging area of the DR PCI system,
the imaging area is configured to move relative to the repeated fringe pattern during the scan, and wherein the x-ray detector is configured to generate a plurality of uncorrelated reference images.

13. The system of claim 12, wherein during the image scan of the imaging area, the imaging area is repeatedly exposed using the x-ray source while moving the imaging area relative to the repeated fringe pattern to generate a set of image data.

14. The system of claim 12, wherein the set of image data are shifted to form a transformed image data set, the repeated fringe pattern moves across the imaging area held stationary, and wherein the transformed image data set and a set of the uncorrelated reference images at least equal in number to the set of transformed image data set are fourier reconstructed to extract at least one of transmission, dark-field, differential phase contrast, and integrated phase images of the object.

15. The system of claim 12, wherein the reference images are collected prior to or after the object scan, or the reference images are stored in advance.

16. The system of claim 12, wherein the fringe pattern is produced by the pitch of the analyzer grating G2 being unequal to the pitch of an interference pattern produced by the phase grating G1 at a position of the analyzer grating G2.

17. The system of claim 12, wherein the fringe pattern is produced by the position of the analyzer grating G2 is offset from a Talbot distance, and wherein the pitch of the analyzer grating G2 is equal to a pitch of the interference pattern.

18. A digital radiographic (DR) phase-contrast imaging (PCI) system comprising:
    a beam shaping assembly comprising a source grating G0;
    an x-ray grating interferometer comprising,
        a phase grating G1, and
        an analyzer grating G2; and
    an area x-ray detector,
    wherein a pitch and a position of the analyzer grating G2 relative to a pitch of an interference pattern produced by the phase grating G1 produce a repeated fringe pattern over a width of the analyzer grating G2, the relative position of the phase grating G1 and the analyzer grating G2 does not change for an image scan of an imaging area of the DR PCI system, the imaging area is configured to move relative to the repeated fringe pattern during the scan, the x-ray detector is configured to generate a plurality of uncorrelated reference images, the object is moved relative to the repeated fringe pattern by holding the interferometer and the x-ray detector fixed relative to each other while moving the imaging area across the interferometer with a step=$np_x/M$, and wherein n is an integer number (1, 2, 3, . . . ), $p_x$ is a detector's pixel pitch and M is an image magnification.

19. The system of claim 12, wherein the DR PCI system is detuned, the relative position of the phase grating G1 and the analyzer grating G2 does not change for a complete scan of the imaging area, and wherein a difference in the analyzer grating G2 pitch and the interference pattern pitch produced by the phase G1 grating at the analyzer G2 grating is sufficient to produce a fringe pattern is greater than 0.1 mm or at least one fringe of moiré pattern over the total width of the analyzer grating G2.

* * * * *